United States Patent [19]

Cox et al.

[11] Patent Number: 5,063,155
[45] Date of Patent: Nov. 5, 1991

[54] METHOD FOR PRODUCING 2'''-O-DEMETHYLTYLOSIN

[75] Inventors: Karen L. Cox, Martinsville; Eugene T. Seno; Gene M. Wild, both of Indianapolis, all of Ind.

[73] Assignee: Eli Lilly and Company, Indianpolis, Ind.

[21] Appl. No.: 173,860

[22] Filed: Mar. 28, 1988

[51] Int. Cl.$^5$ ............... C12N 1/21; C12N 15/52; C12N 15/76; C12P 19/62
[52] U.S. Cl. ................... 435/76; 435/69.1; 435/71.2; 435/91; 435/119; 435/169; 435/172.1; 435/172.3; 435/252.35; 435/320.1; 435/886; 435/74; 536/7.1; 536/27; 935/6; 935/14; 935/22; 935/29; 935/38; 935/39; 935/40; 935/42; 935/59; 935/60; 935/61; 935/75
[58] Field of Search ............ 536/7.1, 27; 435/72, 435/69.1, 119, 71.2, 91, 169, 172.1, 172.3, 75, 76, 77, 78, 79, 252.35, 320.1, 886; 935/6, 14, 22, 29, 38, 39, 40, 42, 59, 60, 61, 75

[56] References Cited

PUBLICATIONS

Chater et al., 1985, Resistance, regulatory and production genes for the antibiotic methylenomycin are clustered, *The EMBO Journal*, 4(7): 1893–1897.
Biological Abstracts Database Abstract No. 85046796; S. E. Fishman et al.: "Cloning genes for the biosynthesis of a macrolide antibiotic" & Proc. Natl. Acad. Sci. USA 1987, vol. 84, No. 23, pp. 8248–8252, *abstract*.
Biological Abstracts Database Abstract No. 76017914; H. A. Kirst et al. "Structure activity studies among 16 membered macrolide antibiotics related to tylosin" & J. of Antibiotics 1982, vol. 35, No. 12, pp. 1675–1682, *abstract*.
Nature 314:642–644 (1985) Hopwood et al.
Nature 309:462–464 (1984) Malpartida and Hopwood.
Antimicrobial Agents and Chemotherapy 20:214–225 (1981) Baltz and Seno.
In Protein Engineering 365 (Inouye and Sarma ed., Academic Press, Inc.), Baltz et al. (1986).
Journal of Antibiotics 36:131 (1982) Baltz, et al.
Journal of Natural Products 49:971 (1986) Cox, et al.
The Journal of Antibiotics 40:1123 (1987) Kiyoshima, et al.

*Primary Examiner*—Richard A. Schwartz
*Assistant Examiner*—Richard C. Peet
*Attorney, Agent, or Firm*—Nancy J. Harrison; Leroy Whitaker

[57] ABSTRACT

The present invention discloses a method for producing a novel antibiotic, 2'''-O-demethyltylosin. The novel antibiotic, utilizing recombinant DNA technology, can be produced from a transformed mutant of a tylosin producing microorganism. By transforming for example *Streptomyces fradiae* GS 16 with plasmid pHJL284, the transformant can produce 2'''-O-demethyltylosin. *Streytomyces fradiae* GS16 is a tylosin producing species that contain a mutation in the tylE gene found in the tylosin biosynthetic pathway. The tylE gene codes for demethylmacrocin 2'''-O-methyltransferase enzyme (DMOMT), the enzyme that methylates the 2-hydroxyl position of the 6-deoxyallose moiety. Plasmid pHJL284 contains the cloned tylF gene which codes for the macrocin 3'''-O-methyltransferase enzxyme (MOMT), the enzyme that methylates the 3'''-hydroxyl position, but it does not contain the tylE gene. Transformation of *S. fradiae* GS16 with plasmid pHJL284 results in increased copies of the tylF gene in the absence of the tylE gene, therefore allowing an increased rate of methylation of the 3'''-hydroxyl position in the absence of the methyl group at the 2'''-hydroxyl position. The resulting transformant, therefore, can produce 2'''-O-demethyltylosin in appreciable quantities. The present invention is not limited to *S. fradiae*. For example, two other tylosin producing species such as *Streptomyces rimosus* and *Streptomyces hygroscopicus*, may also be used for purposes of the invention disclosed. 2'''-O-Demethyltylosin is useful as an antibiotic with a microbial inhibitory activity similar to tylosin.

10 Claims, 5 Drawing Sheets

Tylosin

2'''' -O-demethyltylosin

METHOD FOR PRODUCING 2'''-O-DEMETHYLTYLOSIN

SUMMARY OF INVENTION

The present invention is a new method for producing the novel compound 2'''-O-demethyltylosin. This compound is identical to tylosin except for the absence of the 2'''-O-methyl group on the mycinose moiety of the tylosin molecule.

The present invention discloses a novel compound obtainable by utilizing recombinant DNA technology. Transforming a microorganism containing a mutant tylE gene (demethylmacrocin -2'''-O-methyltransferase gene (DMOMT)) with a plasmid containing a cloned tylF gene (macrocin 3'''-O-methyltransferase gene (MOMT)) allows for the production of 2'''-O-demethyltylosin. The mutation in the DMOMT gene (tylE) normally precludes significant methylation at the 3'''-hydroxyl position by the tylF product, MOMT; but coupled with the higher dosage of the MOMT gene (tylF), it provides for an increased rate of methylation at the 3-position of 6-deoxyallose in the absence of the methyl group at the 2-position. 2'''-O-Demethyltylosin is biologically active and has a spectrum of activity similar to the antibiotic tylosin.

Recently, the development and exploitation of recombinant DNA technology in antibiotic producing organisms has mainly been directed toward the development of cloning vectors for the ultimate production of novel antibiotics. A previous method for obtaining novel antibiotics is mutasynthesis, the feeding of unnatural side chain precursors to an idiotroph genetically blocked in antibiotic biosynthesis. Another method is hybrid biosynthesis in which a wild-type strain is fed an unnatural precursor in the presence of an enzyme inhibitor which phenotypically blocks the biosynthetic pathway of the recipient strain. Protoplast fusion has also been used and is a good method for the interspecific transfer of genetic backgrounds.

While certain hybrid antibiotics have been discussed by Hopwood et al., 1985, in Nature 314:642, the present invention concerns the effective utilization of mutants blocked in the tylosin biosynthetic pathway and not the transfer of biosynthetic genes between Streptomyces species producing different antibiotics. Improved vectors for use in antibiotic-producing organisms were also disclosed in Malpartida and D. A. Hopwood, 1984, Nature 309:462. The present invention, however, is primarily concerned with mutations in the tylosin biosynthetic pathway and cloning of genes in the tylosin biosynthetic pathway.

The application of recombinant DNA technology to an antibiotic biosynthetic pathway was recently described in U.S. patent application Ser. No. 06/842,330 filed Mar. 21, 1986 and which has been continued as Ser. No. 07/351,350 filed May 12, 1989. That application discloses vectors and methods of increasing the antibiotic-producing ability of an antibiotic-producing organism. The method involves providing higher levels, as compared to an untransformed organism, of an enzyme or other gene product that is rate-limiting in an antibiotic biosynthetic pathway. The present invention concerns a new method for producing a novel compound, the antibiotic 2'''-O-demethyltylosin, a compound not previously obtainable from a microorganism in appreciable quantities. Such production can now be obtained by transforming a mutant microorganism with a recombinant DNA vector containing a copy of a specific gene that, in the presence of a specific mutant gene in the tylosin biosynthetic pathway, results in the microorganism producing 2'''-O-demethyltylosin.

2'''-O-Demethyltylosin, a heretofore unknown compound, has been discovered in trace amounts in the mutant Streptomyces fradiae GS16 strain. The present invention, however, utilizing recombinant DNA technology allows for the production of 2'''-O-demethyltylosin in appreciable quantities. The present invention is particularly significant in that it allows for the further application of recombinant DNA technology to Streptomyces. Because over two-thirds of the known natural antibiotics are produced by Streptomyces, it is especially desirable to develop methods that are applicable to this industrially important group.

For purposes of the present invention as disclosed and claimed herein, the following terms are as defined below.

Antibiotic-Resistance-Conferring Gene—a DNA segment that encodes an activity that confers resistance to an antibiotic.

Recombinant DNA Cloning Vector—any selectable and autonomously replicating or chromosomally integrating agent, including but not limited to plasmids and phages, comprising a DNA molecule to which additional DNA can be or has been added.

rep—as used in the Figures herein, a plasmid origin of replication.

Restriction Fragment—any linear DNA generated by the action of one or more restriction enzymes.

Transformant—a recipient host cell, including the viable protoplast thereof, that has undergone transformation.

Transformation—the introduction of DNA into a recipient host cell, including the viable protoplast thereof, that changes the genotype of the recipient cell.

Tylosin Biosynthetic Gene—a DNA segment that encodes an enzymatic activity, or encodes a product that regulates expression of an enzymatic activity, that is necessary for an enzymatic reaction in the process of converting primary metabolites to antibiotic intermediates, which can also possess antibiotic activity, and then to tylosin.

Blocked Mutant—an organism that produces little or no tylosin because of a mutational defect, including but not limited to a deletion, in one or more tylosin biosynthetic genes.

Tylosin Biosynthetic Pathway—the entire set of tylosin biosynthetic genes and biochemical reactions necessary for the process of converting primary metabolites to antibiotic intermediates and then to tylosin.

DETAILED DESCRIPTION OF THE INVENTION

The present invention is a method for producing 2'''-O-demethyltylosin by a microorganism, said method comprising, a) transforming a mutant strain of a tylosin producing species of Streptomyces, said strain containing a mutation that prevents the expression of tylosin biosynthetic gene tylE, with a recombinant DNA cloning vector which comprises DNA which codes for the expression of tylF gene in said mutant strain and b) culturing said strain transformed with said vector under conditions suitable for cell growth, expression of tylF, and subsequent production of 2'''-O-demethyltylosin.

The invention further comprises recombinant DNA cloning vectors and 2'''-O-demethyltylosin producing microorganisms transformed with the aforementioned genes and vectors as well as the novel antibiotic, 2'''-O-demethyltylosin. 2'''-O-demethyltylosin is useful as an antibiotic with a microbial inhibitory activity similar to the tylosin antibiotic.

The present invention is best constructed by transforming *Streptomyces fradiae* GS16 with plasmid pHJL284. *Streptomyces fradiae* GS16 is a blocked mutant which fails to produce tylosin because of a mutation in the tylE gene. The tylE mutation prevents O-methylation at the 2''' position of the mycinose precursor, 6-deoxy-D-allose, attached to the lactone ring. Therefore, without the tylE gene, the 2''' position contains a hydroxyl group. The tylE gene is responsible for the 2'''-O-methylation because the tylE gene codes for the enzyme demethylmacrocin 2'''-O-methyltransferase (DMOMT). Since efficient methylation of the 3'''-hydroxyl position by the tylF product, macrocin 3'''-O-methyltransferase (MOMT), requires previous methylation of the 2'''-hydroxyl position, *Streptomyces fradiae* GS16 produces 2'''-O-demethyltylosin in only trace amounts. *Streptomyces fradiae* GS16 has been deposited and can be obtained from the American Type Culture Collection (ATCC), Rockville, Md. 20852, under the accession number ATCC 31664.

Plasmid pHJL284, a vector useful in producing the new antibiotic of the present invention contains the tylF gene of the tylosin biosynthetic pathway. The tylF gene codes for the macrocin 3'''-O-methyltransferase (MOMT) enzyme. With the presence of the higher level of MOMT, in the absence of DMOMT activity (therefore no methyl group at the 2'''-O-position) an increased rate of methylation at the 3'''-O-position of 6-deoxyallose is observed. Plasmid pHJL284 can be obtained from *E. coli* K12 HB101/pHJL284, a strain deposited and made part of the permanent stock culture collection of the Northern Regional Research Laboratory (NRRL), Peoria, Ill. 61604. It is available as a stock reservoir of the plasmid under the accession number NRRL B-18044.

To better appreciate the present invention, one must understand how tylosin is biosynthesized in tylosin-producing microorganisms. Tylosin is composed of a 16-member branched lactone (tylonolide) to which three sugars (mycarose, mycaminose, and mycinose) are attached. The lactone is derived from two acetates, five propionates, and a butyrate by condensation of a propionyl-S-coenzyme A molecule with two malonyl-S-coenzyme A molecules, four methylmalonyl-S-coenzyme A molecules, and an ethylmalonyl-S-coenzyme A molecule by a scheme believed analogous to that involved in fatty acid biosynthesis. This process requires the product of the tylG gene. Lactone formation, sugar biosynthesis/attachment, and the conversion of resultant intermediate compounds to tylosin are catalyzed by a series of gene-encoded enzymes. The cloning and/or mutating of genes that code for such enzymes allows for the manipulation of this biosynthetic pathway.

Figure 1:
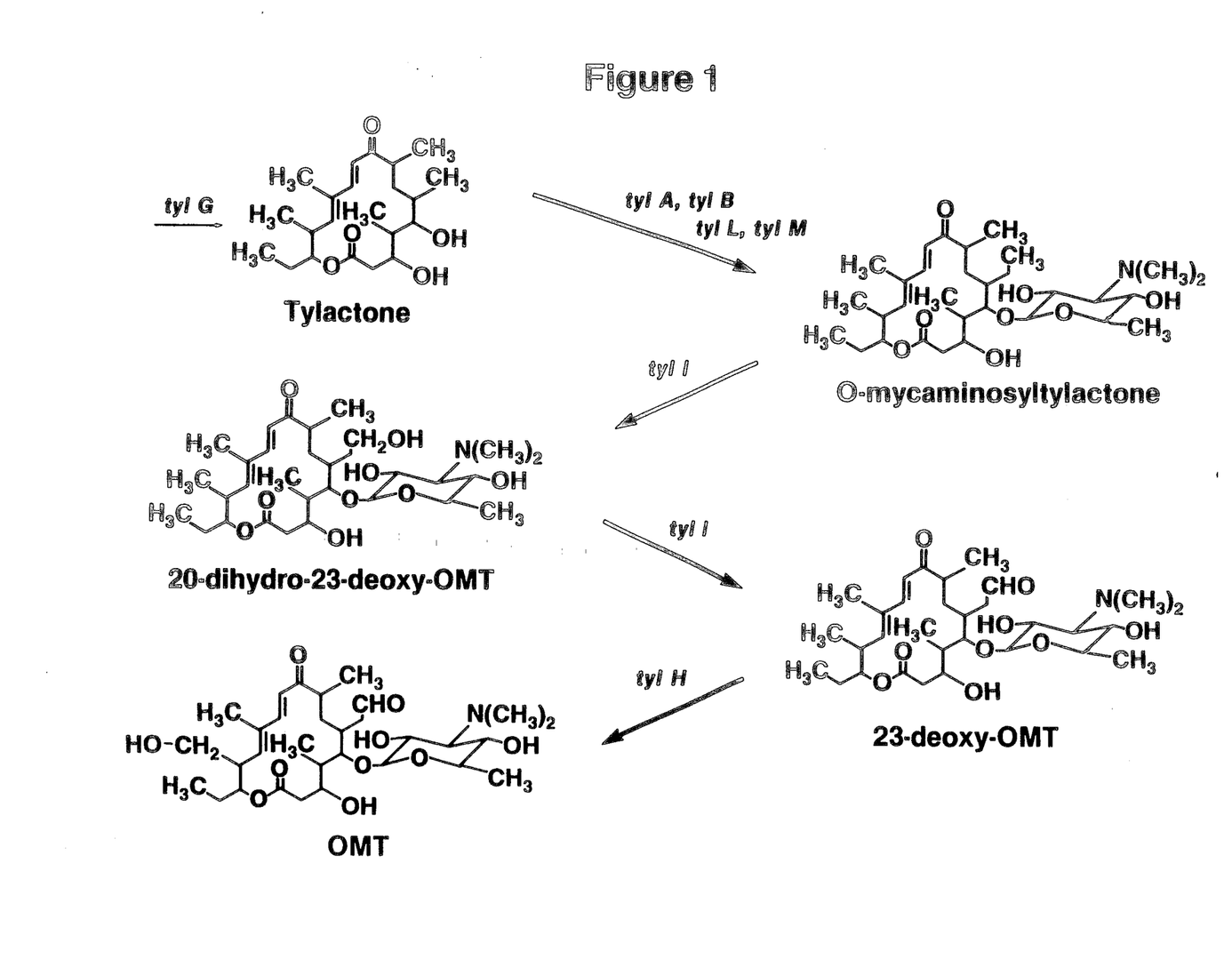
FIG. 1: Tylosin Biosynthetic Pathway from Tylactone to Tylosin
Figure 1A:
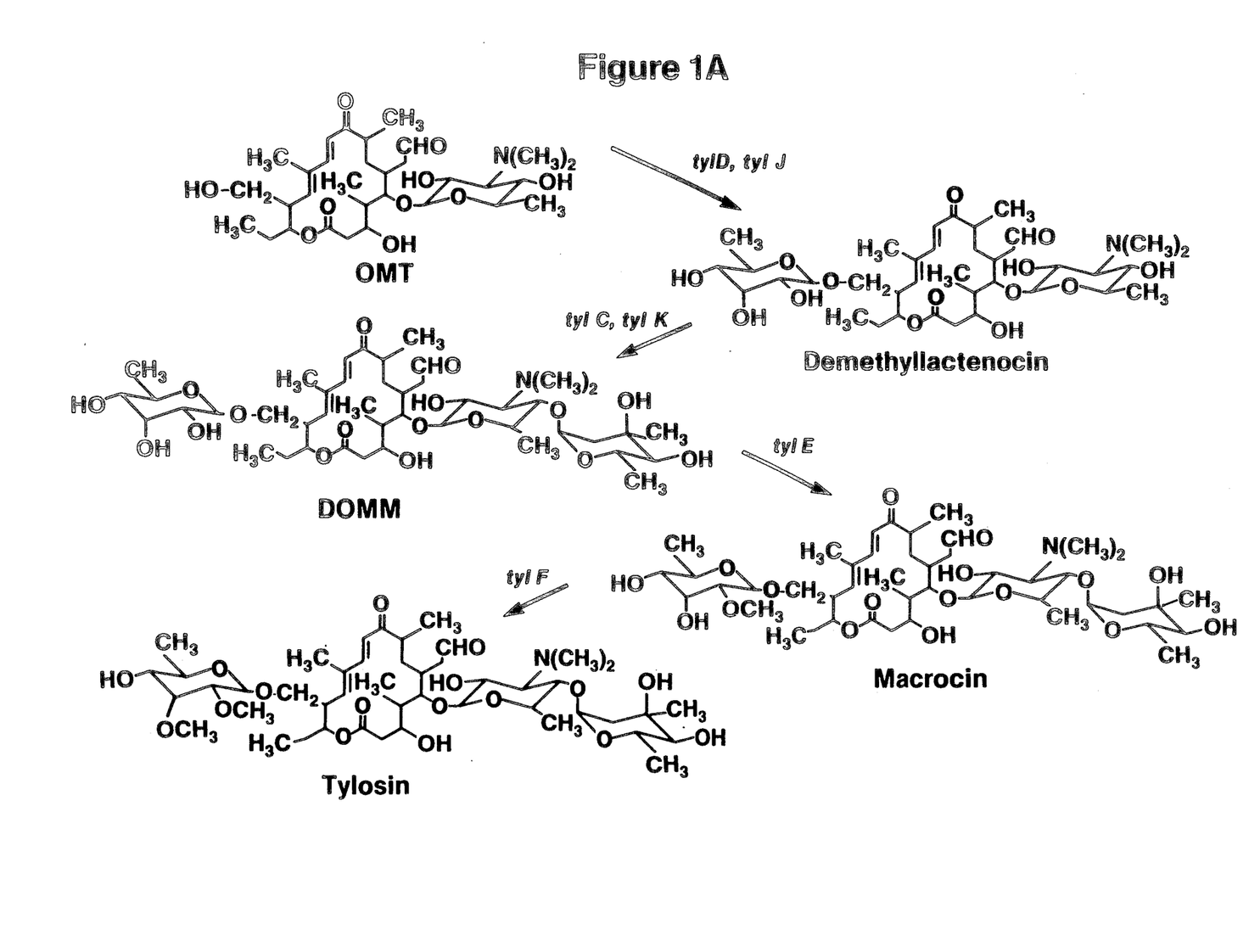
Figure 2:
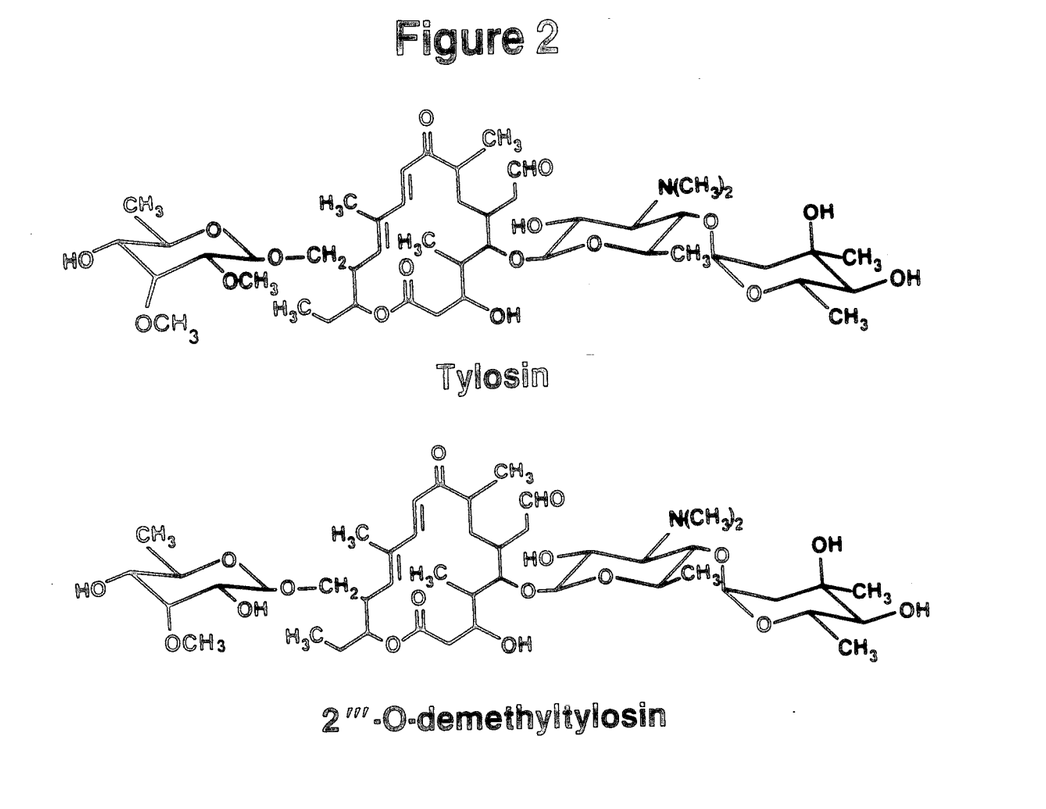
FIG. 2: 2'''-O-demethyltylosin and Tylosin
Figure 3:
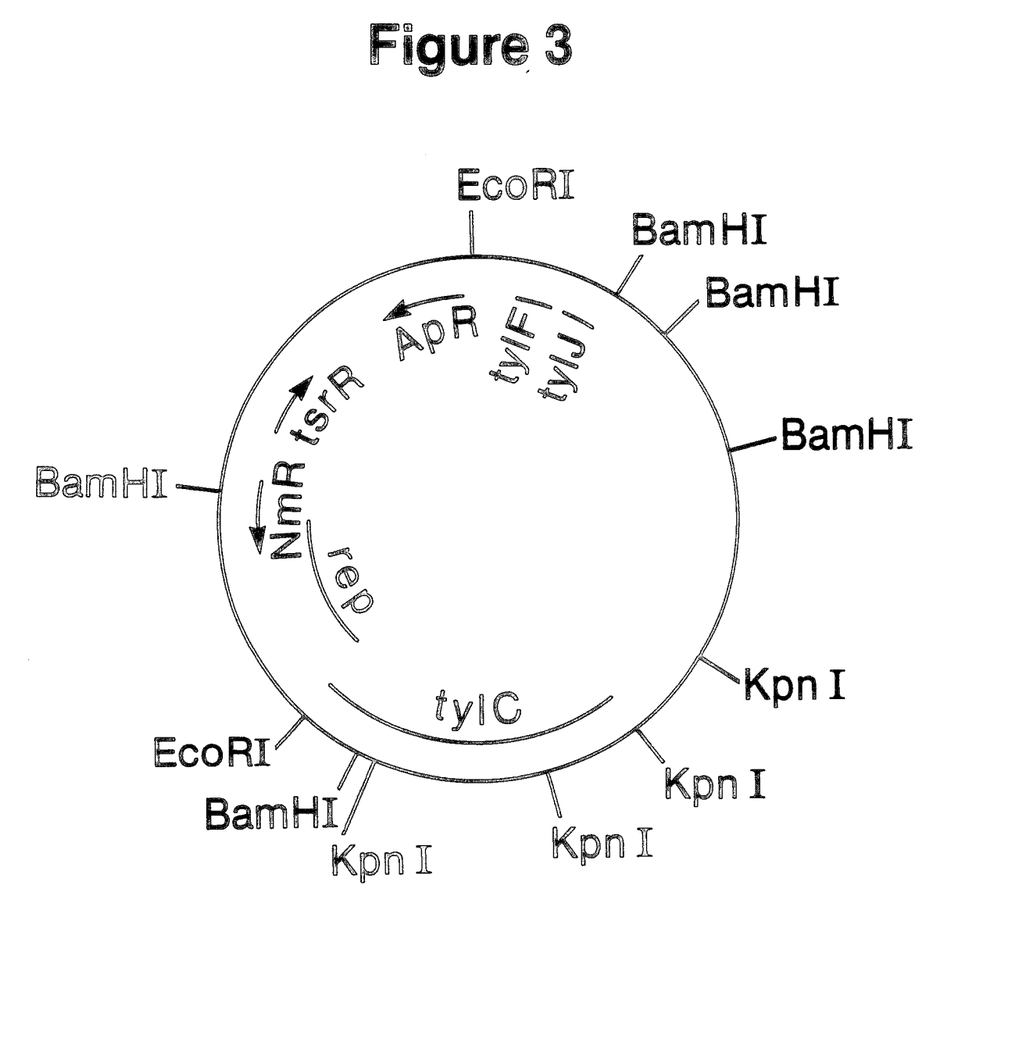
FIG. 3: Restriction Site Map of Plasmid pHJL284

Analysis shows that tylosin is assembled by a series of biosynthetic steps. Studies have shown that tylactone, the first recognizable intermediate excreted by *Streptomyces fradiae*, is converted to tylosin by a preferred sequence of reactions which include: (1) addition of mycaminose to the C-5 hydroxyl position of the lactone; (2) oxidation of the C-20 methyl group to a hydroxymethyl group; (3) dehydrogenation of the C-20 hydroxymethyl group to a formyl group; (4) oxidation of the C-23 methyl group to a hydroxymethyl group; (5) addition of 6-deoxy-D-allose to the C-23 hydroxymethyl group; (6) addition of mycarose to the 4'-hydroxyl group of mycaminose; (7) addition of a methyl group to the 2'''-hydroxyl position of demethylmacrocin (DOMM), and (8) addition of a methyl group to the 3'''-hydroxyl position of macrocin to produce tylosin. Genes that are required for the preferred sequence of reactions converting tylactone to tylosin include, but are not limited to tylA, tylB, tylL, tylM, tylI, tylH, tylD, tylJ, tylK, tylC, tylE, and tylF. A schematic representation of the tylosin biosynthetic pathway is presented in FIG. 1 of the accompanying drawings; each arrow in FIG. 1 represents a conversion step requiring the biosynthetic gene products indicated by the gene name(s) located above the corresponding arrow.

As previously described, the new compound of the present invention is obtained by transforming a tylosin producing Streptomyces containing a mutation in the tylE gene with a r-DNA cloning vector which comprises the tylosin biosynthetic gene tylF. Various methods for isolating antibiotic biosynthetic genes such as, for example, tylF, are now well known in the art. For instance, Example 1 below is a preferred method for isolating Streptomyces chromosomal and plasmid DNA which is generally applicable to all antibiotic-producing organisms. After chromosomal or plasmid DNA is isolated from a particular antibiotic-producing organism, a genomic library of the prepared DNA can be constructed in accordance with methods that are also well known in the art. For purposes of illustration, Example 2 discloses a preferred method for preparing a genomic library that increases the likelihood that an entire antibiotic biosynthetic pathway will be cloned. After the genomic library is constructed, DNA fragments containing antibiotic biosynthetic genes can be identified by a number of methods. For example, a DNA probe can be constructed based on the knowledge of at least part of the amino acid sequence of an antibiotic biosynthetic enzyme. This probe can then be hybridized to the library by standard procedures to detect DNA fragments containing the gene which codes for the enzyme. Another method is to introduce the cloned DNA fragments into mutants blocked in antibiotic biosynthesis, and screen for restoration of antibiotic production. Depending upon the vector in which the library was prepared, the DNA may be directly transformed into the mutants, or first subcloned into an appropriate vector using standard procedures.

Those skilled in the art will recognize that the new compound of the present invention is not limited solely to production in *Streptomyces fradiae*. For example, *Streptomyces rimosus* and *Streptomyces hygroscopicus* are two other microorganisms that naturally produce tylosin by virtue of a tylosin biosynthetic pathway. Therefore, both of these microorganisms may also be used to obtain the new compound of the present invention. Upon inducing mutations in the tylE gene, these organisms can be used as hosts for purposes of the present invention. Thus, any tylosin producing strain containing the tylE mutation can be converted to a 2'''-O-demethyltylosin producer by transformation with cloning vehicles comprising a tylF gene capable of expression. Treatment of Streptomyces with N-methyl-N'-nitro-N-nitrosoguanidine (MNNG) can be carried out in substantial accordance with the mutagenesis procedure of Baltz and Seno (1981) in Antimicrobial Agents and Chemotherapy 20:214–225. The mutagenesis procedure will result in the generation of the desired Streptomyces tylE blocked mutant strains.

Alternative methods for transforming microorganisms for purposes of the present invention include classical methods of genetic recombination such as, for example, protoplast fusion, conjugation and transduction. Any of these methods could be used to introduce tylF genes into the mutant background. In addition, those skilled in the art will recognize that the present invention is not limited to the use of plasmid pHJL284 or any other particular vector. Any vector capable of replication and maintenance or integration in Streptomyces fradiae, Streptomyces rimosus, Streptomyces hygroscopicus or any other tylosin producing organism can be modified to carry the appropriate tylosin biosynthetic gene and therefore used to produce 2'''-O-demethyltylosin. Such vectors into which tylosin biosynthetic genes can be ligated include, but are not limited to, pIJ702, pIJ903, pIJ922, and pIJ941. Plasmid pIJ702 may be obtained from the American Type Culture Collection, Rockville, Md., 20852 under the accession number ATCC 39155. Plasmids pIJ903, pIJ922, and pIJ941 may be obtained from the John Innes Streptomyces Culture Collection, John Innes Institute, Colney Lane, Norwich, England NR4 7UH, under the respective accession numbers, 3417, 3419, and 3338. Plasmids pHJL284 and pHJL311 contain various tylosin biosynthetic genes, including tylF, and are on deposit at the Northern Regional Research Laboratory (NRRL), Peoria, Ill. 61604, with the respective accession numbers B-18044 and B-18046. These vectors replicate in S. fradiae and are thus useful in the present method for producing 2'''-O-demethyltylosin. Table 1 provides a brief description of plasmids used to exemplify the method of the present invention.

TABLE 1

| Plasmids Comprising Tylosin Biosynthetic Genes | | |
|---|---|---|
| Host/ Designation | Tylosin Gene(s) | NRRL Accession No. |
| E. coli K12 HB101/pHJL284 | C,F,J | B-18044 |
| E. coli K12 HB101/pHJL311 | C,F,J,K,H | B-18046 |

As previously indicated, transformation of Streptomyces fradiae GS16 with plasmid pHJL284, which contains the wild-type tylF gene, results in production of 2'''-O-demethyltylosin in appreciable amounts. The higher level of the MOMT gene product in the absence of DMOMT activity allows an increased rate of methylation at the 3-position of 6-deoxyallose in the absence of the methyl group at the 2-position. Although not bound or limited by theory, applicants believe that this explains why S. fradiae GS16 makes 2'''-O-demethyltylosin in trace amounts and why the transformants produce it in appreciable quantities. Thus, S. fradiae GS16/pHJL284 is a particularly preferred strain for purposes of the present invention.

Plasmid pHJL284 is introduced into Streptomyces fradiae GS16 by protoplast transformation. Plasmid pHJL284 carries an antibiotic resistance conferring gene (resistance to thiostrepton to which S. fradiae GS16 is sensitive), thereby allowing transformants to be selected by regenerating the protoplasts in the presence of thiostrepton. After an appropriate transformant has been identified, it is propagated only in the presence of thiostrepton to maintain the plasmid. To produce 2'''-O-demethyltylosin, the transformant is grown under tylosin fermentation conditions which have been previously described in U.S. Pat. No. 4,419,447. The fermentation broth is filtered and extracted as described for demycinosyltylosin in U.S. Pat. No. 4,419,447, incorporated herein by reference. The extracted material, which is a mixture of 2'''-O-demethyltylosin and the precursor, 2'''-O-demethylmacrocin, is further purified to obtain pure 2'''-O-demethyltylosin as described in Example 11. Further details of the transformation, culture, and fermentation procedures are found in the Examples as later presented.

2'''-O-Demethyltylosin has a spectrum of activity which is substantially equivalent to tylosin. Thus, 2'''-O-demethyltylosin has inhibitory action against growth of various microbial organisms including both gram-positive and gram-negative bacteria and certain microbial plant pathogens. The specific antimicrobial activity associated with tylosin is disclosed in U.S. Pat. No. 3,178,341, such patent being incorporated herein by reference. The majority of microorganisms against which 2'''-O-demethyltylosin has inhibitory action are gram-positive. 2'''-O-Demethyltylosin like tylosin, is well tolerated in animals and effective by both the oral and subcutaneous routes.

The following examples further illustrate and detail the invention disclosed herein but are in no way intended to limit the scope of the invention. Both an explanation of and the actual procedures for constructing the invention are described where appropriate.

EXAMPLE 1

DNA Isolations from Streptomyces

A. Culture of Streptomyces fradiae

A culture of Streptomyces fradiae was grown at 30° C. in 10 ml. of trypticase soy broth (TSB*) by inoculating a single colony into 10 ml. of broth and homogenizing this solution three times until the colony is disrupted. The 10 ml. culture was grown for 48 hours and then homogenized and used to inoculate a flask containing 500 ml. of TSB supplemented with glycine to a final concentration of 0.4%. The culture was grown for 48 hours at 30° C. and the mycelia collected by centrifugation at 10,000 rpm for 15 minutes in Sorvall centrifuge bottles using a RC-5 Sorvall and a GSA rotor. About 50 grams of wet mycelia were produced.

*Trypticase soy broth is obtained from Baltimore Biological Laboratories, P.O. Box 243, Cockeysville, Md. 21031 or Difco Laboratories, Detroit, Mich.

The cell pellet was resuspended in 500 ml. of Tris-sucrose (10mM Tris-HCl pH 8.0/1.0mM EDTA/25% sucrose). Next, the suspension was supplemented with 250 ml. of 0.25M EDTA (pH 8.0) and 250 ml. of lysozyme solution [10 mg./ml. lysozyme (Calbiochem) in Tris-sucrose solution]. This mixture was incubated at room temperature for 15 minutes and then 50 mg. of proteinase K (Beckman) was added and the suspension incubated for an additional 30 minutes. About 50 ml. of a 20% w/v solution of sodium dodecylsulfate (ultra-pure obtained from Gallard-Schlesinger Chemical Mfg. Corp., 584 Mineola Place, New York City, N.Y. 11514) was added, gently mixed, and then the lysed cells were incubated at 55° C. for 30 minutes. After 250 ml. of 5M NaCl was gently mixed into the lysed cell solution, the suspension was transferred to Sorvall centrifuge tubes (~40 ml./tube) and placed on ice for 2 hours. The solution was centrifuged at 15,000 rpm for 20 minutes in a Sorvall SS34 rotor and centrifuge. The supernatants were pooled together (~700 ml.) and 0.64 volume of isopropyl alcohol was added and mixed gently. This solution was transferred to Sorvall centrifuge bottles and the precipitates collected by centrifugation at 10,000 rpm in a Sorvall GSA rotor and centrifuge. The precipitates were air dried and then gently resuspended in TE to a final volume of 100 ml.

About 5.0 mg. of RNAase A (obtained from Sigma, St. Louis, Mo.) was suspended in 1 ml. TE (10mM Tris-HCl pH 8.0/1.0mM EDTA), boiled for two minutes, added to the above DNA suspension together with 5.0 mg of proteinase K and then the mixture was incubated at 4° C. for 15 hours. Next, an equal volume of buffer saturated phenol was added to the mixture and the phases separated by centrifugation (5,000 rpm, GSA rotor, 10 minutes). The aqueous layer was decanted into a 250 ml. graduated cylinder and adjusted to 0.3M NaOAc by the addition of 3M NaOAC (pH 8.0). This solution was placed on ice and 2 volumes of cold ethanol was gently added to avoid mixing the two liquids. Using a procedure developed by Marmur et al., 1961, J. Mol. Biol. 3:208-218, the high molecular weight DNA species were collected by gently swirling a glass rod at the interface between the DNA and ethanol. The thus collected DNA was washed once in 70% ethanol and air dried prior to resuspension in 5 ml. TE (supplemented to 0.1M NaCl) to a final concentration of 1.4 mg./ml.

EXAMPLE 2

Preparation of Lambda Charon 4 DNA

A. Preparation of Lambda Charon 4 Vector

An overnight culture of *Escherichia coli* K12 C600$R_k^-M_k^-$(ATCC 33525) was grown at 37° C. in 10 ml. of T broth (10 gm. Bacto-Tryptone, 5 gm. yeast extract, 5 gm. NaCl and distilled water to 1 liter, pH 7.0) supplemented with maltose (20% maltose to 0.2%) and MgSO$_4$ (1M MgSO$_4$ to 10 mM). Supplemented broth is designated TMM. A phage stock of Charon 4, (ATCC 40432) a standard *E. coli* K12 lambda cloning vector was serially diluted and 0.1 ml. of the individual phage dilutions were added to 0.1 ml. of a 1/10 dilution of the *E. coli* culture grown in TMM. These cultures were then incubated at 37° C. for 20 minutes. After 3 ml. of TM top agar (T broth plus 10mM MgSO$_4$ and 0.7% agar) were added, the cultures were plated on T agar (T broth + 1.5% agar) supplemented with 10mM MgSO$_4$ and incubated at 37° C. for 16-24 hours. A plate containing ~20,000 pfu (plaque-forming units) was selected and flooded with 5 ml. of lambda buffer (6.35 gm. Tris-HCl, 1.18 gm. Tris base, 2.46 gm. MgSO$_4$.7H$_2$O, 5.84 gm. NaCl and distilled water to 1 liter). The plate was scraped into a 50 ml. Sorvall tube and after the addition of 0.1 ml. CHCl$_3$, the tube was centrifuged at 4,000 rpm for 10 minutes. The supernatant was collected in a fresh tube and 0.5 ml. CHCl$_3$ was added. It should be noted that 3-5 lysates may be made to obtain the proper titer.

B. Preparation of Phage Lysate

A 20 ml. culture of *E. coli* K12 C600$R_k^-M_k^-$(ATCC 3525) was grown in TMM broth at 37° C. overnight. This culture was mixed with $10^9$ pfu of Charon 4 (from the plate lysates of Example 2A and titered according to conventional methods) and incubated at 30° C. for 10 minutes without shaking. The incubated mixture was divided in half and each half was added to a 1 liter flask containing 500 ml. of T broth supplemented with 1M MgSO$_4$ to a final concentration of 10mM MgSO$_4$ and shaken at 37° C. until lysis (about 3-8 hours).

After lysis, DNase I [(10 mg./ml. in 50mM Tris-HCl, pH 8.0), obtained from Worthington Diagnostic, Freehold, N.J. 07728] was added to a final concentration of 1 µg./ml. per flask and the flasks were shaken for 15 minutes. Next, 7.9 gm. NaCl/100 ml. was added to each flask and shaken into solution. After 0.2 ml. of chloroform was added per flask, the contents were transferred to Sorvall centrifuge bottles and spun in a GSA rotor at 4,000 rpm for 10 minutes. After pooling the supernatants, polyethylene glycol 6000 (obtained from Sigma) was added to a final concentration of 100 gm./l., shaken into solution and placed in an ice bath for 1 hour.

Aliquots of this solution were transferred to Sorvall bottles and the precipitates were collected by centrifugation in a GSA rotor for 10 minutes at 6,000 rpm. All pellets were resuspended in a total volume of 15 ml. of lambda buffer and transferred to a 50 ml. Sorvall tube containing 15 ml. of chloroform and vortexed before centrifugation at 4,000 rpm for 10 minutes.

After the upper aqueous phase was collected, cesium chloride (0.814 gm./ml.) was added and adjusted to obtain a refractive index of 1.3809. The solution was transferred to Beckman ultracentrifuge tubes and spun to equilibrium (18 hr., 50,000 rpm). The phage band was extracted with a needle and syringe and dialyzed against 2 liters of lambda buffer for 4-8 hours. After the approximate DNA concentration was determined, lambda DNA was extracted by the addition and gentle mixing of an equal volume of buffer-saturated (50 mM Tris-HCl pH 8.0) phenol [Ultra-pure obtained from Bethesda Research Laboratory (BRL) Gaithersburg, Md, 20877]. The phases were separated by centrifugation in a Sorvall centrifuge and the aqueous layer removed and mixed with an equivalent volume of ether. The phases were again separated by centrifugation and the ether layer removed and discarded. After the ether extraction step was repeated, the lambda DNA solution was made 0.3M NaOAc by the addition of 3M NaOAc pH 8.0. The DNA was precipitated by the addition of 2 volumes cold ethanol and stored overnight at $-20°$ C. The DNA was collected by centrifugation (15,000 rpm, 15 minutes, Sorvall tubes), washed once with 70% ethanol and air dried. This DNA pellet was resuspended in 500 µl. TE to a final concentration of ~400 µg./ml.

C. Preparation of Charon 4 EcoRI Arms

To obtain both the left and right arms of Charon 4, 250 µl. of Charon 4 DNA (100 µg.), 30 µl. 10X EcoRI buffer (1000 mM Tris-HCl pH 7.5, 500 mM NaCl, and 50 mM MgCl$_2$), 30 µl mg/ml bovine serum albumin (BSA) and 10 µl. distilled water were digested with 10 µl. [(100 units) New England Biolabs, Inc., 32 Tozer Road, Beverly, Mass. 01915] EcoRI enzyme for 2 hours at 37° C. An additional 10 µl. of EcoRI enzyme was added and incubated for another hour. The reaction was terminated by increasing the temperature to 70° C.

for 10 minutes. An equal volume of buffer saturated phenol was mixed in and the phases separated by centrifugation in a microfuge. The aqueous layer was removed and extracted twice with ether as described in the preceding example.

The DNA suspension was divided in half and added to two SW40 tubes containing 10–40% w/v sucrose (in 1M NaCl, 20 mM Tris-HCl pH 8.0, and 5 mM EDTA) gradients containing 2 μg./μl. ethidium bromide essentially as described in Maniatis et al., 1982, Molecular Cloning, Cold Spring Harbor Laboratory, Cold Spring Harbor, N.Y. After running in a Beckman SW40 rotor for 15 hours at 25,000 rpm at 5° C., the bands were visualized by UV light and the four visible bands extracted with a syringe and needles. The ethidium bromide was extracted with n-butanol and the resulting DNA examined by agarose gel electrophoresis (AGE). The two bands representing the left and right arms of Charon 4 were mixed equimolar, diluted in half, precipitated by the addition of two volumes of ethanol and stored at −20° C. overnight. The DNA precipitate was collected by centrifugation in an HB4 rotor (Sorvall tube, 12,000 rpm, 30 minutes) and then resuspended in TE to a final concentration of 0.174 μg./l. Charon 4 arm DNA.

EXAMPLE 3

Preparation of *Streptomyces fradiae* DNA

A. Culture of *Streptomyces fradiae* and Preparation of DNA Suspension

A culture of *Streptomyces fradiae* was grown under conditions and DNA prepared in substantial conformance with Example 1.

B. Collection of High Molecular Weight Fractions

Approximately one-half ml. of the DNA suspension from part A above was layered onto the top of four SW40 Beckman polyallomer tubes containing a 5–20% w/v sucrose gradient made in substantial accordance with the teaching of Example 2C with the exclusion of ethidium bromide and the substitution of 5% w/v and 20% w/v sucrose solutions for the respective 10% w/v and 40% w/v sucrose solutions. These gradients were run for 17 hours at 30,000 rpm using a Beckman SW40 rotor in a Beckman ultracentrifuge. One-half ml. fractions were collected from each tube by puncturing the bottom of the tube and collecting the drops. The fractions were examined by AGE (agarose gel electrophoresis)and the high molecular weight fractions (>50 kb) were pooled and precipitated by conventional methods. The DNA precipitate was resuspended in 500 μl. TE to a final concentration of 1.4 μg./μl.

C. Preparation of the *Streptomyces fradiae* Insert DNA

About 0.5 ml. of the DNA from the preceding example was adjusted to 0.3M NaOAc by the addition of 3M NaOAc and precipitated with 2 volumes cold ethanol and stored at −20° C. overnight. The precipitate was collected by centrifugation, washed in ethanol and resuspended in 1.6 ml. TE to a final concentration of 0.46 μg./μl. and held at 4° C. for 16 hours. Three reactions were set up to digest the DNA with HaeIII restriction enzyme and three reactions were set up to digest the DNA with AluI restriction enzyme.

1. HaeIII Restriction Enzyme Digestions

The HaeIII reaction mixture was set up containing about 540 μl. of the suspended DNA, 250 μl. 10X HaeIII buffer (500 mM NaCl, 60 mM MgCl$_2$, 60 mM β-mercaptoethanol), 1700 μl. water, and 8.9 μl. of a 1/10 dilution of HaeIII enzyme (7 units/μl. BRL) in 1X HaeIII buffer. Three reactions, each containing ~800 μl., were prepared from the single HaeIII reaction mixture and incubated at 37° C. for 20 minutes, 40 minutes, and 60 minutes and then placed on ice. The extent of digestion was monitored by AGE. To each reaction, 2 μl. of a 1/10 dilution of HaeIII restriction enzyme was added and incubation for 30 minutes at 37° C. continued. The reactions were again placed on ice and the extent of digestion was monitored by AGE. This 2 μl. enzyme addition was repeated, and the extent of the final digestion was monitored by AGE. The three reactions were pooled together, made 0.3M NaOAc by the addition of 3M NaOAc, rinsed with 2 volumes ethanol and precipitated overnight at −20° C.

2. AluI Restriction Enzyme Digestions

The same procedure with respect to the HaeIII digestions was used for a similar digestion with AluI except that 10 μl. of a 1/10 dilution of AluI (6 units/μl. BRL), ~1700 μl. of distilled water and 10X AluI buffer (500 mM Tris-HCl pH 8.0, 50 mM MgCl$_2$, 500 mM NaCl, and 10 mM dithiothreitol) were used in place of the HaeIII reaction enzyme and buffer. The three reactions were run in substantial accordance with the teaching of the HaeIII digestions with the exception that only one additional incubation period with AluI enzyme was required. These reactions then were pooled and precipitated.

The two DNA digestions were separately collected by centrifugation (12,000 rpm, 12 minutes) in a HB4 rotor. The precipitates were washed once with 70% ethanol. Finally, the precipitates were resuspended separately in 200 μl. TE. The suspensions were pooled, and TE was added to a final volume of 600 μl. About 200 μl. of this pooled DNA was added to each of three, 13 ml. 5–20% w/v sucrose gradients. These three gradients were run for 17 hours in a SW40 Beckman rotor at 30,000 rpm at 5° C. About 30 fractions, containing ~0.4 ml. each, were collected from each tube by puncturing the bottoms of the gradient tubes and collecting drops. Each fraction was analyzed on AGE and those corresponding to DNA in the size range of 10–25 kb DNA were pooled and precipitated by conventional methods. The precipitate was resuspended in 800 μl. TE at a concentration of 0.065 μg./μl.

3. Methylation of *Streptomyces fradiae* DNA

About 200 μl. of 5X EcoRI methylase buffer (500 mM) Tris-HCl pH 8.0, 12.5 mM dithiothreitol, 25 mM EDTA, 2 mg./ml. BSA, and 5.5μM S-adenosyl-methionine) and 10 μl. EcoRI methylase (10 units/μl. BRL) were added to the ~800 μl. of DNA prepared above and then incubated at 37° C. for 2 hours. The DNA was extracted twice with buffer saturated phenol and the phenol layer was re-extracted with TE. The aqueous phases were pooled and extracted twice with ether and then precipitated with sodium acetate followed by two volumes of ethanol and incubated at −20° C. for 2 hours. The precipitate was collected by centrifugation (12,000 rpm, 15 minutes) and the DNA washed once in 70% ethanol, air dried, and then resuspended in 75 μl. of TE. This contained approximately 44 μg. of methylated AluI-HaeIII partially digested *S. fradiae* DNA.

4. Linker Addition

About 40 μl. of EcoRI linker (pGGAATTCC obtained from Collaborative Research, Inc., 128 Spring Street, Lexington, Mass. 02173) at 100 μg./ml. in TE was incubated at 65° C. for three minutes and then cooled on ice. A ligation reaction containing 70 μl. of methylated *Streptomyces fradiae* DNA, 40 μl. linker DNA, 40 μl. 5X ligase/kinase buffer (250 mM Tris-HCl pH 7.8, 25% glycerol, 25 mM dithiothreitol, and 50 mM $MgCl_2$), 40 μl. 0.66M ATP and 12 μl. (1 unit/μl. Boehringer-Mannheim Biochemicals) T4 DNA ligase were incubated at room temperature for 12 hours. The reaction was terminated by increasing the temperature to 65° C. for five minutes and then stored at 4° C. overnight. About 190 μl. of the stored ligation reaction was mixed with 45 μl. 10X EcoRI buffer, 195 μl. distilled water and 20 μl. EcoRI enzyme (10 units/μl. BRL) and incubated at 37° C. for five hours. After the addition of 20 μl. 0.25M EDTA (pH 8.0), the reaction was terminated by increasing the temperatures to 65° C. for five minutes followed by cooling on ice. This reaction was layered onto a 5–30% w/v sucrose gradient and run in a SW40 rotor (18 hours, 30,000 rpm, 5° C.). The tube was punctured at the bottom and 36 five drop fractions were collected. The fractions were examined by AGE and those fractions ranging in size from 10 to 19 kb were pooled, precipitated with sodium acetate and ethanol and stored overnight at −20° C. The DNA precipitates were collected by centrifugation in a Sorvall HB4 rotor (12,000 rpm, 15 minutes), washed once in 70% ethanol, air dried and resuspended in 400 μl. TE. This suspension constitutes the EcoRI linked *S. fradiae* DNA at a concentration of 0.022 μg./μl.

EXAMPLE 4

Production of Phage Library

About 2 μg. of the *Streptomyces fradiae* DNA, prepared in Example 3(C), were mixed with 17.2 μl. (~3 μg.) Charon 4 arms, prepared in Example 2C, and then the DNA was precipitated by the addition of 3M sodium acetate (to a final concentration of 0.3M NaOAc) and two volumes of ethanol. This mixture was incubated at −70° C. for 15 minutes. The DNA pellet was collected by centrifugation in a Brinkman microfuge for 10 minutes, washed in 70% ethanol and air dried. Next, the pellet was resuspended in 16 μl. of the following ligation reaction mixture: 4 μl. 5X kinase/ligase buffer, 4 μl. 0.66M ATP pH 7.4, 11 μl. distilled water, and 1 μl. T4 DNA ligase; this ligation reaction was incubated at 9° C. for 72 hours.

The ligation was conventionally packaged using Bethesda Research Laboratory packaging extract in substantial accordance with the manufacturer's specification. Other such in vitro packaging mixes, such as, Biotec packaging kit, are available for use in the present application. The packaging mixture was loaded onto a CsCl block gradient and run in a SW50 Beckman rotor (2 hours, 30,000 rpm, 5° C.). The cesium chloride gradients were made in substantial accordance with the teaching of Maniatis et al., 1982, except that the density per 0.5 ml. of CsCl were 1.7, 1.5 and 1.3. The tube was punctured at the bottom and 10-drop fractions were collected and dialyzed individually in a BRL mini-dialysis unit against lambda buffer. The fractions were titered as described in Example 2A using a 10 ml. culture of *E. coli* K12 294 (ATCC 31446) in TMM for 16–24 hours at 37° C., instead of *E. coli* K12 $C600R_k^-M_k^-$, and examined for recombinants. Recombinants were identified by the appearance of non-blue plaques as revealed on T agar plates supplemented with 10 mM $MgSO_4$ and 40 μg./ml. 5-bromo-4-chloro-3-indolyl-β-D-galactosidase (X-gal from BRL). The various fractions were pooled to give a library of recombinant phages. Amplification of the primary lysate was made by preparing plate lysates of the library on *E. coli* K12 294 where at least 4,000 recombinant plaques were on each plate. From these plate lysates a large scale phage lysate and DNA prep were done as taught in Example 2. The DNA was resuspended in 1 ml. TE at a concentration of 0.23 μg./μl.

EXAMPLE 5

The Use if a Radioactive Synthetic Oligonucleotide to Detect DNA Sequences Containing the tylF Gene in the Lambda Charon 4 Library The amplified phage lysate is plated on *E. coli* K12 294 as described in Example 2A to give about 5,000 plaques per plate and a total of about 20,000 plaques. The plaques are transferred to nitrocellulose filters by the method of Benton and Davis, *Science*, 196:180 (1977) as described in detail in the laboratory manual, *Molecular Cloning* (T. Maniatis, E. F. Fritsch, J. Sambrook, Cold Spring Harbor Laboratory, Cold Spring Harbor, N.Y., 1982, pp. 320–321). To detect the tylF gene in the library, a radioactive oligonucleotide probe is constructed based upon the known DNA sequence (Fishman et al., Proc. Natl. Acad. Sci. USA 84:8248, 1987) of part of the gene which codes for the first 36 amino acids of the tylF gene product, MOMT. The method of making the DNA probe, which should be at least 44 nucleotides long for best results, is well known to those skilled in the art. Briefly, the oligonucleotides are synthesized by the phosphotriester method using a SAMI automated DNA synthesizer (Biosearch, San Rafael, Calif.) or equivalent instrument. The system is automated so the user need only determine the DNA sequence desired and then follow the instructions for use of the instrument. The resulting oligonucleotides are purified by gel electrophoresis in 15% acrylamide and 7.0M urea. The synthetic oligonucleotides are end labeled with [γ-$^{32}$P] ATP and polynucleotide kinase as described in: Maniatis, Fritsch and Sambrook, *Molecular Cloning: A Laboratory Manual* (Cold Spring Harbor Laboratory, Cold Spring Harbor, N.Y., 1982). The radioactive probe is hybridized to the filter as described in detail in the *Molecular Cloning* manual, pp. 324–328.

The phages in plaques which hybridize to the probe are grown to high titer as described in Example 2A, and phage DNA is prepared as described in Example 2B.

EXAMPLE 6

Culture of *E. coli* K12 $C600R_k^-M_k^-$/pHJL210 and Isolation of Plasmid pHJL210

A single bacterial colony of *E. coli* K12 $C600R_k^-M_k^-$/pHJL210 (NRRL B-15824) was inoculated into LB medium which contains, per liter aqueous solution, 10 gm. Bacto tryptone, 5 gm. Bacto yeast extract and 10 gm. NaCl (pH 7.5) with 25 μg./ml. of ampicillin according to conventional microbiological procedures. The culture was incubated at 37° C. for 16–24 hours. The following morning, 500 ml. of M9 medium (Miller et al., 1979, Experiments in Molecular Genetics, Cold Spring Harbor Laboratories, Cold Spring Harbor, N.Y.) supplemented to 1 mM MgSO$_4$, 0.2% glucose, 0.3-4% CAA (casamino acids, Difco), 2 μg./ml. B1 (thiamine-HCl, Sigma) and additives were inoculated with 5 ml. of the culture. The culture was incubated with vigorous shaking at 37° C. for 16-24 hours and samples of the culture were inoculated at dilutions of 1/10 to 1/50 into the supplemented M9 media and incubated with vigorous shaking at 37° C. for 2½ to 3 hours. The turbidity of the culture measured with the blue filter was approximately 300 to 400 Klett units. Chloramphenicol (150-175 μg./ml.) was added to the culture and incubation with vigorous shaking was continued for 16-24 hours.

The bacterial cells were harvested by centrifugation at 7500 rpm for 5 minutes at 4° C. and then washed twice with 200 ml. of SV (0.15M NaCl, 0.1M NaEDTA pH 8.0). The pellet was resuspended in 10 ml./gm. wet ht TS solution (25% sucrose, 50 mM Tris, pH 8) and placed on ice. To this suspension, 2 ml./gm. wet weight of lysozyme solution (5 mg./ml. in 50 mM Tris-HCl pH 7.8) was added and left to chill on ice for 5 minutes. Next, 4 ml./gm. wet weight of 0.25M EDTA pH 8.0 was added and chilled for another 5 minutes. Upon the addition of 16 ml./gm. wet weight lysis solution (0.4% deoxycholate, 1% Brij 58, 50 mM Tris and 0.0625M EDTA, pH 8) the mixture was incubated at 37° C. for 15-30 minutes. The debris was removed by centrifugation in a Sorvall SS34 rotor at 21,000 rpm for 15-30 minutes at 4° C. The supernatant was saved and 0.1 vol. of 3M NaOAc, at pH 8 and 0.64 volumes isopropyl alcohol were added to the supernatant. The solution was centrifuged at 10,000 rpm for 10 minutes at 4° C., whereupon the pellet was resuspended in 1 ml of TE (10 mM Tris, 1mM EDTA pH 8). The plasmid DNA was purified by centrifugation to equilibrium in cesium chloride (CsCl) density gradients containing propidium diiodide according to known techniques.

EXAMPLE 7

Subcloning *Streptomyces fradiae* DNA From The Recombinant Bacteriophages Which Hybridized To The Probe A. Digestion of Plasmid pHJL210

About 10 μl. (~11 μg.) of plasmid pHJL210 (prepared in Example 6) was added to 5 μl. 10X EcoRI buffer, 5 μl. BSA, 25 μl. distilled water and 5 μl. of EcoRI restriction enzyme (10 units/ml. NEB) and incubated for two hours at 37° C. The reaction was terminated by raising the temperature to 70° C. for 10 minutes. The DNA was precipitated by addition of 6 μl. 3M NaOAc pH 8 0 and 120 μl. cold ethanol. After incubation at −70° C. for 15 minutes, the DNA was collected by centrifugation in a Brinkman microfuge for 10 minutes. The DNA pellet was washed once with 70% ethanol, air dried and then resuspended in 80 μl. distilled H$_2$O. This suspension was supplemented with 20 μl. 5X CIAP buffer (500 mM Tris-HCl pH 7.5, 250 mM NaCl and 50 mM MgCl$_2$). To dephosphorylate the DNA, 3 μl. of a 1/10 dilution of calf intestinal alkaline phosphatase, Grade III (4 units/μl. Boehringer Mannheim) prepared in accordance with the manufacturer's specification, was added and the reaction incubated first at 37° C. for 30 minutes and then at 70° C. for an additional 30 minutes.

B. Preparation of the *Streptomyces fradiae* DNA Inserts

About 10 μl. (~2 μg.) of the DNA from each bacteriophage (prepared in Example 2) was incubated with 2 μl. 10X EcoRI buffer, 2 μl. BSA, 5 μl. water, and 1 μl. EcoRI enzyme (10 units/μl. NEB) for three hours at 37° C. The reaction was terminated by increasing the temperature to 70° C. for 10 minutes.

C. Ligation

About 10 μl. of the dephosphorylated and EcoRI-digested pHJL210 DNA was added to the 20 μl. EcoRI-digested bacteriophage DNA and the mixture precipitated with 3 μl. 3M NaOAc and 82 μl. cold 100% ethanol. After incubation at −70° C. on dry ice for 10 minutes, the precipitate was collected by centrifugation, washed once with 70% ethanol and air dried. The pellet was resuspended in 23 μl. distilled water and to this solution, 8 μl. 0.66M ATP, 8 μl. 5X kinase/ligase buffer and 1 μl. ligase (Boehringer-Mannheim) were added and the ligation incubated at 15° C. for 20 hours. The ligation was diluted to promote circularization by the additions of ~48 μl. distilled water, 16 μl. 5X kinase/ligase buffer, 16 μl. 0.66M ATP and 1 μl. ligase. The solution was incubated for 72 hours at 15° C. and then the reaction terminated by raising the temperature to 70° C. for 10 minutes. The DNA was precipitated by adding 12 μl. 3M NaOAc and 300 μl. cold ethanol to each tube. The tube was incubated on dry ice for 10 minutes and then the DNA was collected in a Brinkman microfuge, washed once with 70% ethanol, air dried and finally resuspended in 30 μl. TE.

EXAMPLE 8

Isolation of Plasmid pHJL284 (Alternative to Example 7)

A. Culture of *E. coli* K12 HB101/pHJL284

Lyophils of *E. coli* K12 HB101/pHJL284 can be obtained from the NRRL under the accession number NRRL B-18044. The lyophilized cells are streaked onto L-agar plates (L agar contains 10 gm. of Bacto Tryptone, 5 gm. of Bacto Yeast Extract, 10 gm. of NaCl, 2 gm. of glucose, and 15 gm. of agar per liter) containing 50 μg./ml. ampicillin to obtain a single-colony isolate of *E. coli* K12 HB101/pHJL284. One such colony was used to inoculate 100 ml. of LB medium (LB medium is L agar without the agar) and plasmid DNA was prepared as described in Example 6.

EXAMPLE 9

Construction of Plasmid pXYZ1000

A. EcoRI/BamHI Digestion of pHJL401

About 2 μg. of plasmid pHJL401 (isolated and prepared as described in Example 6 from NRRL B-18217) is suspended in a total volume of 25 μl. of EcoRI buffer (50 mM NaCl, 100 mM Tris-HCl (pH 7.5), 50 mM MgCl$_2$, 100 μg./ml. bovine serum albumin) plus 1 μl. of 16 μ./μl. EcoRI restriction enzyme from New England Biolabs. The reaction is incubated at 37° C. for four hours, and then terminated by heating to 70° C. for 10 minutes. The restricted DNA is precipitated by addition of 2.5 volumes of absolute ethanol and 0.1 volume of 3M sodium acetate, and maintained at −70° C. for 15 minutes. The precipitate is collected by centrifugation and resuspended in 25 μl. of BamHI restriction enzyme buffer (150 mM NaCl, 6 mM Tris-HCl, pH 7.9, 6 mM MgCl$_2$, 100 μg./ml. bovine serum albumin) plus 2 μl. of 8 units/μl. BamHI restriction enzyme from New England Biolabs. The reaction is incubated at 37° C. for four hours and terminated by heating at 70° C. for 10 minutes. The restricted DNA is maintained at 0° C. until use.

B. EcoRI/BamHI Digestion of pHJL284

About 5 μg. of pHJL284 DNA, prepared in substantial accordance with the teaching of Example 8 is digested with EcoRI and BamHI restriction enzymes as described in Example 9A except that the reactions are done in 50 μl. volumes rather than 25 μl. The resulting fragments are separated by agarose gel electrophoresis, and the 2.3 kb fragment containing tylF and tylJ genes is isolated by standard procedures. The isolated fragment is maintained at 0° C.

C. Ligation of EcoRI/BamHI Digested pHJL401 with the 2.3 kb EcoRI/BamHI Fragment Containing TylF and TylJ The EcoRI/BamHI digested pHJL401 and the 2.3 kb EcoRI/BamHI fragment are mixed together and precipitated by addition of 0.1 volume of 3M NaOAc and 2.5 volumes of absolute ethanol. The precipitate is dissolved in 50 μl. ligase-kinase buffer (25M Tris-HCl, pH 7.8, 50 mM $MgCl_2$, 25 mM dithiothreitol and 25% glycerol). Twelve μl. of 0.66M ATP and two μl. of T4 DNA ligase are added and the solution is incubated at 15° C. for 18 hours.

D. Transformation of GS16

Figure 4:
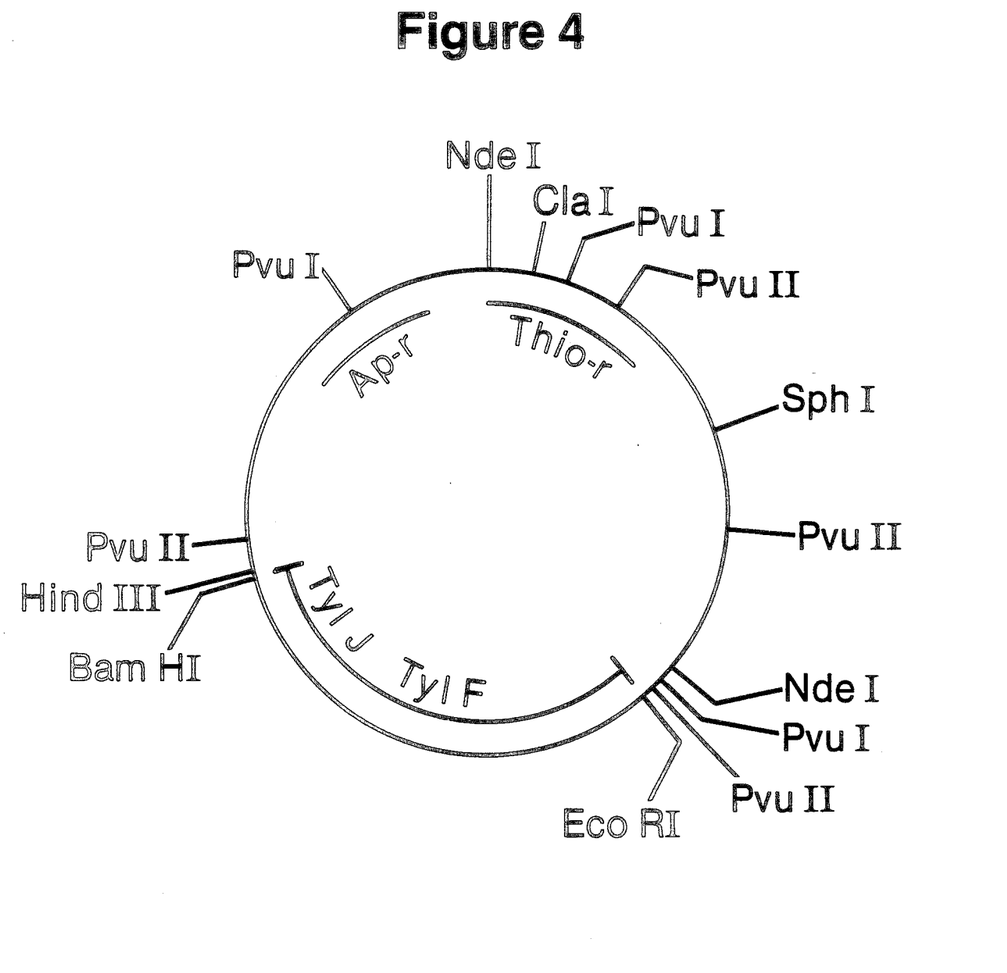
FIG. 4 Restriction Site Map of Plasmid pXYZ1000.

The ligation reaction is terminated by incubation at 70° C. for 10 minutes, and the DNA is precipitated by addition of 0.1 volume of 3M NaOAc and the 2.5 volume of absolute ethanol and maintained at −70° C. for 15 minutes. The precipitate, which contains plasmid pXYZ1000 is dissolved in 20 μl. of TE, and 10 μl. is used to transform GS16 in accordance with the procedure described in Example 10. Thiostrepton-resistant transformants are screened for production of 2'''-O-demethyltylosin, and plasmid DNA from these colonies is analyzed to confirm the correct plasmid structure. A map of plasmid pXYZ1000 is shown in FIG. 4 of the accompanying drawings.

EXAMPLE 10

Construction of *Streptomyces fradiae* GS16/pHJL284

The plasmid DNA, constructed in Example 7, can be transformed directly into GS16 but a more efficient method involves first amplifying the plasmid DNA and confirming its structure in *E. coli*. A large amount of the desired plasmids can then be purified from *E. coli* and used to transform the *Streptomyces fradiae* strains. The methods for introducing plasmid DNA into *E. coli* by transformation, identifying the plasmid by restriction enzyme analysis, and purifying large quantities of plasmid from *E. coli* are common and well known to those skilled in the art. After the appropriate plasmids (i.e., those with the DNA inserts which were detected by hybridization to the oligonucleotide probe) have been purified, about 5 μg. of each is transformed into GS16.

A culture of *Streptomyces fradiae* GS16 (ATCC 31664) was inoculated into 20 ml. of trypticase-soy broth (TSB) and incubated in a water-bath incubator at 29° C. at 260 rpm for 16–24 hours. The culture was homogenized using a homogenizing vessel (Thomas Scientific, Swedesboro, N.J.) and a T-Line laboratory stirrer and then fragmented using a Sonifier Cell Disruptor (Head Systems Ultrasonics, Inc.) for 7 seconds at 76 Watts. Four ml. of the homogenized, fragmented culture were inoculated into 20 ml. of TSB (BBL) containing 0.3% weight by volume glycine, and the culture was again incubated for 16–24 hours at 29° C. Then the culture was homogenized and recultured as described above. After this third incubation, the culture was homogenized, collected, and then washed twice with P medium. P medium base was prepared by adding 103 gm. of sucrose to 0.25 gm. of $K_2SO_4$ and 2.03 gm. of $MgCl_2.6H_2O$ and then adding deionized water to a final volume of 700 ml. The mixture was then sterilized, and to each 70 ml. of solution, about 10 ml. each of 0.05 gm. $KH_2PO_4$/100 ml. of deionized water; 2.78 gm. $CaCl_2$/100 ml. of deionized water; and 0.25 M TES (2-([tris-(hydroxymethyl)methyl]-amino)-ethanesulfonic acid) at a pH=7.2 were added to form the desired P medium.

The cell pellet was resuspended in 15 ml. of P medium containing 1 mg./ml. lysozyme (Calbiochem, La Jolla, Calif. 92037) and then incubated at room temperature for about one and one-half hours to form protoplasts. The protoplasts were gently collected by centrifugation, washed twice with P medium, resuspended in 2ml. of P medium, and incubated on ice until use. About 5 μg. of plasmid pHJL284 DNA was added to about 50 μl. of 1 mg./ml. heparin sulfate (Sigma) in P medium and incubated on ice for about 10 minutes. Much less plasmid DNA, about 5–100 nanograms, can be used to transform *Streptomyces fradiae* strains if such DNA is first replicated in a *S. fradiae* host rather than used directly from an *E. coli* strain. The procedure for isolating Streptomyces plasmid DNA is well known and also described in Hopwood et al., 1985, Genetic Manipulation of Streptomyces: *A Laboratory Manual* (John Innes Foundation, Norwich, England). The DNA/heparin solution was first added to about 200 μl. of protoplasts, and about 0.9 ml. of a solution composed of 55% PEG 1000 (Sigma) in P medium was then added to the DNA/protoplast mixture, and the resulting mixture was gently mixed at room temperature.

The mixture was plated in varying aliquots onto R2 plates using 4 ml. of soft R2 agar overlays. R2 plates contain 30 ml. of R2 media and have been dried at 37° C. for about 4 days. R2 medium is prepared by adding 103 gm. sucrose, 0.25 gm. $K_2SO_4$, 2 ml. of trace element solution, 10.12 gm. $MgCl_2.6H_2O$, 10.0 gm. of glucose, 2.0 gm. of L-asparagine, 0.1 gm. of Casamino acids, and 22 gm. of agar to 700 ml. of water; sterilizing the resulting solution; and finally, adding 100 ml. of each of the following solutions: 0.05 gm. $KH_2PO_4$/100 ml. of deionized water; 2.22 gm. $CaCl_2$/100 ml. of deionized water; and 0.25 M TES, pH=7.2. The pH of the final solution is adjusted to equal 7.2 with NaOH. Trace element solution contains 40 mg. $ZnCl_2$, 200 mg. $FeCl_3.6H_2O$, 10 mg. $CuCl_2.2H_2O$, 10 mg. $MnCl_2.4H_2O$, 10 mg. $Na_2B_4O_7.10H_2O$, and 10 mg. $(NH_4)_6Mo_7O_{24}.4H_2O$ per liter. The soft-R2-agar overlays are prepared by adding 51.5 gm. of sucrose, 5.06 gm. $MgCl_2.6H_2O$, 1.11 gm. $CaCl_2$, 50 ml. of 0.25 M TES at a pH=7.2, and 2.05 gm. agar to enough deionized water to achieve a final volume of 500 ml. The mixture is steamed to melt the agar, distributed into tubes (4 ml. each), and autoclaved prior to use. After the transformed protoplasts had been plated, the plates were incubated at 29° C. for 24 hours, and then, 4 ml. of soft R2 agar containing 25 μl. of 50 mg./ml. thiostrepton in dimethylsulfoxide (E. R. Squibb, Princeton, N.J. 08540) were spread over the protoplasts. Incubation of the plates at 29° C. was continued until regeneration was complete, usually a period of about 7–14 days, to select for the desired *Streptomyces fradiae* GS16/pHJL284 transformants. The *S. fradiae* GS16/pHJL284 strain was cultured under the fermentation conditions described in U.S. Pat. No. 4,419,447, such disclosure incorporated herein by reference, except that the media were supplemented with 20 μg./ml. of thiostrepton to maintain the plasmid. 2‴-O-Demethyltylosin production was conventionally assayed and determined in substantial accordance with the teaching of Baltz and Seno, 1981, *Antimicrobial Agents and Chemotherapy*, 20:214–225; and Kennedy, J. H., 1983, *Journal of Chromatography*, 281:288–292.

EXAMPLE 11

A. Structure Confirmation of 2‴-O-Demethyltylosin

2‴-O-Demethyltylosin has an $R_f$ of approximately 0.42–0.52 by thin layer chromatography on silica gel plates developed with a solution of 95% ethyl acetate and 5% diethylamine. This $R_f$ is much greater than the $R_f$ (0.06) of the compound 2‴-O-demethylmacrocin, which is produced by *Streptomyces fradiae* GS16 without the cloned tylF gene. The 2‴-O-demethyltylosin can also be identified by its retention time (about 690 seconds) in a High Pressure Liquid Chromatography (HPLC) system consisting of a Zorbox C8/PN (523) column and a mobile phase consisting of 23% acetonitrile, 19% tetrahydrofuran, and 58% ion-pair solution (1.45 grams of pentane-sulfonic acid, 58 ml. of glacial acetic acid and 5800 ml. of water). The system is isocratic and run at 30° C. The 2‴-O-demethyltylosin is detected by absorbance at 280nm. The retention time of 2‴-O-demethylmacrocin in this system is about 480 seconds.

B. Preparation of 2‴-O-Demethyltylosin from Fermentation Broth

Culture broth from a 7-day fermentation of *Streptomyces fradiae* GS16 (pHJL284) was filtered to remove the mycelium and medium solids. The pH of the filtrate was adjusted to 9.0–9.5, the macrolide components were extracted into ethyl acetate, and then back extracted into water at pH 4.0. The pH was raised to 9.0 and the macrolide components were extracted into methylene chloride. The solvent was evaporated to dryness, and the solid residue was dissolved in amylacetate at a concentration of about 50 g./l. The solution was stirred with an equal volume of saturated sodium borate at H 9.0. The amylacetate fraction was recovered and the macrolide components were extracted into water at pH 4.0–4.5; the pH was adjusted to 9.0 and the activity was re-extracted into methylene chloride. The methylene chloride was evaporated and the residue was dissolved in ethyl acetate. 2‴-O-Demethyltylosin was separated from other macrolide components by preparative thin layer chromatography on silica gel using a developing solvent consisting of 95% ethyl acetate and 5% diethylamine. 2‴-O-Demethyltylosin has the greatest $R_f$ ($\approx 0.42$–0.52) of the macrolide components present in the mixture. The resulting pure 2‴-O-demethyltylosin is dissolved in ethyl acetate at 1 mg./ml. for use as a reference standard.

EXAMPLE 12

Generation and Identification of a tylE Mutant of *Streptomyces fradiae*

A preserved specimen of a tylosin producing strain of *Streptomyces fradiae* (e.g., ATCC 19609) is inoculated into 20 ml. of TSB and grown aerobically for 24–48 hours at 30° C. until well grown. The culture is homogenized and sonicated (see Example 21), and 5 ml. is inoculated into 45 ml. of TSB. The culture is grown aerobically for 16–24 hours, again fragmented, and 5 ml. aliquots are inoculated into 45 ml. of TSB in several replicate flasks. The cultures are grown for 2.5–3 hours aerobically at 37° C., the pH is adjusted to 8.5 with sodium hydroxide, and then 25 μg./ml. of chloramphenicol and different amounts of N-methyl-N'-nitro-N-nitrosoguanidine (MNNG) are added to produce final concentrations of 100, 200, or 300 μg./ml. of MNNG. The cultures are grown for 20 minutes, samples are removed to test viability, and the remaining cells are pelleted by centrifugation and resuspended in fresh TSB. The cultures are grown for 16–24 hours at 37° C. The cultures which exhibit reasonably good growth after incubation are homogenized, sonicated, diluted in TSB and plated to obtain isolated mutagenized colonies on AS1 medium (yeast extract, 1 gm./l.; L-alanine, 0.2 gm./l.; L-arginine, 0.2 gm./l.; L-asparagine, 0.5 gm./l.; soluble starch, 5 gm./l.; sodium chloride, 2.5 gm./l.; $Na_2SO_2$, 10 gm./l.; Meer agar, 20 gm./l.; pH 7.5 before sterilizing). The plates are incubated for 7–14 days at 29–30° C. to allow colony growth. Individual colonies are inoculated into small flasks or bottles containing 7–10 ml. of tylosin fermentation medium (Baltz and Seno, *Antimicrobial Agents and Chemotherapy*, 20:214–225, 1981). A copy patch of each colony is simultaneously made on another AS1 plate. The fermentation cultures are grown aerobically at 29° C. for 7 days and the individual fermentation broths are analyzed by thin layer chromatography for the presence of macrolide components as previously described (Baltz and Seno, 1981). 2‴-O-Demethyltylosin can be initially identified by co-chromatography with known samples of 2‴-O-demethyltylosin (Example 11). The mutant (tylE) producing this compound is then preserved and used for production of 2‴-O-demethyltylosin.

EXAMPLE 13

Construction of *Streptomyces fradiae* BA2 Mutant

*Streptomyces fradiae* is mutated in accordance with Example 12 and the resultant tylE mutation-containing organisms conventionally selected in substantial accordance with Baltz and Seno (1981), in Antimicrobial Agents and Chemotherapy, 20:214–225. The resultant strain is designated as *S. fradiae* BA2 and is useful as a host for purposes of the present invention.

EXAMPLE 14

Construction of Streptomyces rimosus BA3 Mutant

The procedure for obtaining a mutant in the tylosin biosynthetic pathway of *Streptomyces rimosus* (ATCC 10970) is carried out in substantial accordance with the teaching of Example 12 except that *Streptomyces rimosus* is used instead of *Streptomyces fradiae*. A mutation involving the tylE biosynthetic gene can be conventionally identified and selected in accordance with the principles disclosed in Baltz and Seno (1981), in Antimicrobial Agents and Chemotherapy, 20:214–225. The resultant strain is designated as *S. rimosus* BA3 and is useful as a host for purposes of the present invention.

EXAMPLE 15

Construction of Streptomyces hygroscopicus BA4 Mutant

The procedure for obtaining a mutant in the tylosin biosynthetic pathway of Streptomyces hygroscopicus (ATCC 10976) is carried out in substantial accordance with the teaching of Example 12 except that S. hygroscopicus is used instead of Streptomyces fradiae. A mutation involving the tylE biosynthetic gene can be conventionally identified and selected in accordance with the principles described in Baltz and Seno (1981), in Antimicrobial Agents and Chemotherapy, 20:214-225. The resultant strain is designated as S. hygroscopicus BA4.

EXAMPLE 16

The construction of Streptomyces rimosus BA3/pXYZ1000

The construction of Streptomyces rimosus BA3/pXYZ1000 is carried out in substantial accordance with the teaching of Example 10 except that a culture of S. rimosus BA3 and plasmid pXYZ1000 is used instead of Streptomyces fradiae GS16 and plasmid pHJL284. 2'''-O-Demethyltylosin production is conventionally assayed and determined in substantial accordance with the teaching of Baltz and Seno, 1981, in Antimicrobial Agents and Chemotherapy 20:214-225; and Kennedy, J. H., 1983, Journal of Chromatography 281:288-292. The compound is identified initially by its co-chromatography with a known sample of 2'''-O-demethyltylosin (Example 11).

EXAMPLE 17

Construction of Streptomyces hygroscopicus BA4/pXYZ1000

The construction of Streptomyces hygroscopicus BA4/pXYZ1000 is carried out in substantial accordance with the teaching of Example 10 except that a culture of S. hygroscopicus BA4 and plasmid pXYZ1000 is used instead of Streptomyces fradiae GS16 and plasmid pHJL284. 2'''-O-Demethyltylosin production is conventionally assayed and determined in substantial accordance with the teaching of Baltz and Seno, 1981, in Antimicrobial Agents and Chemotherapy 20:214-225; and Kennedy, J. H., 1983, Journal of Chromatography 281:288-292. The compound is identified initially by its co-chromatography with a known sample of 2'''-O-demethyltylosin (Example 11).

EXAMPLE 18

Construction of Streptomyces fradiae BA2/pXYZ1000

The construction of Streptomyces fradiae BA2/pXYZ1000 is carried out in substantial accordance with the teaching of Example 10 except that a culture of S. fradiae BA2 and plasmid pXYZ1000 is used instead of S. fradiae GS16 and plasmid pHJL284. 2'''-O-Demethyltylosin production is conventionally assayed and determined in substantial accordance with the teaching of Baltz and Seno, 1981, in Antimicrobial Agents and Chemotherapy 20:214-225; and Kennedy, J. H., 1983, Journal of Chromatography 281:288-292. The compound is identified initially by its co-chromatography with a known sample of 2'''-O-demethyltylosin (Example 11).

EXAMPLE 19

Integration Of Plasmid pHJL284 Into The Streptomyces Fradiae GS16 Genome For Improved Production of 2'''-O-Demethyltylosin Streptomyces fradiae GS16 is transformed with pHJL284 and thiostrepton resistant transformants are selected as described in Example 10. A transformant, in which the presence of pHJL284 has been verified, is selected and inoculated into TSB plus thiostrepton (20 μg./ml.). The culture is shaken at 30° C. until fully grown (about 48 hours). The culture is homogenized in a glass homogenizer (Thomas Scientific, Swedesboro, N.J.) and fragmented by treatment with ultrasonic vibration (Heat Systems Ultrasomes, Inc.;/cm probe; 7 seconds at 76 watts). Inoculum from this culture is then serially passaged 3 times in TSB without thiostrepton. After each passage, the culture is fragmented and inoculated at a level of 10% of volume. Following the final passage, the culture is fragmented and plated on AS1 agar medium (see Example 12 for composition) containing 25 μg./ml. of thiostrepton. A thiostrepton-resistant colony is picked and grown in TSB. When fully grown, the culture is fragmented and the plating efficiency on medium containing thiostrepton is determined. If the efficiency is at or near a value of 1.00, the pHJL284 plasmid has integrated into the genome, because the autonomous plasmid is unstable and is lost during growth in the absence of antibiotic selection. If the efficiency of plating is much less than 1.00, a thiostrepton resistant colony is picked and the growth in the absence of selection is repeated to again assess the efficiency of plating on thiostrepton. This procedure is repeated until an efficiency of plating equal to or near 1.00 is obtained, indicating that a culture containing pHJL284 integrated into the genome has been obtained. This culture is then used to produce 2'''-O-demethyltylosin by the method described in Example 10.

We claim:

1. A method for producing 2'''-O-demethyltylosin by a microorganism that is a mutant of a tylosin-producing species of Streptomyces fradiae containing a mutation that prevents the expression of tylosin biosynthetic gene tylE, comprising:
   a) transforming the strain with a recombinant DNA cloning vector that comprises DNA which codes for the expression of Streptomyces fradiae tylF in the strain; and
   b) culturing the transformed strain under conditions suitable for cell growth, expression of tylF, and subsequent production of 2'''-O-demethyltylosin.

2. The method of claim 1 wherein said recombinant DNA cloning vector is maintained during the culturing step as an autonomously replicating vector.

3. The method of claim 2 wherein the recombinant DNA cloning vector is a plasmid.

4. The method of claim 3 wherein the plasmid is selected from the group consisting of plasmids pHJL284 and pXYZ1000.

5. The method of claim 4 wherein the plasmid is pHJL284.

6. The method of claim 1 wherein the microorganism is Streptomyces fradiae GS16.

7. The transformant of claim 1 which is Streptomyces fradiae/pHJL284.

8. The transformant of claim 1 which is Streptomyces fradiae/pXYZ1000.

9. The transformant of claim 1 which is Streptomyces fradiae GS16/pHJL284.

10. The transformant of claim 1 which is Streptomyces fradiae GS16/pXYZ1000.

* * * * *